United States Patent
Nichols

(10) Patent No.: US 7,866,320 B2
(45) Date of Patent: Jan. 11, 2011

(54) NASAL CANULA AND MOUTHPIECE ASSEMBLY AND METHOD

(76) Inventor: Heath C. Nichols, 151 N. Maple St., Apt. 110, Burbank, CA (US) 91505-4260

( * ) Notice: Subject to any disclaimer, the term of this patent is extended or adjusted under 35 U.S.C. 154(b) by 976 days.

(21) Appl. No.: 11/148,856

(22) Filed: Jun. 8, 2005

(65) Prior Publication Data

US 2006/0278232 A1    Dec. 14, 2006

(51) Int. Cl.
*A61M 16/00* (2006.01)
(52) U.S. Cl. .............. 128/207.18; 128/207.14; 128/204.18; 128/912
(58) Field of Classification Search ............ 128/207.18, 128/203.22, 203.29, 206.28, 200.14, 203.12, 128/203.18, 204.18, 206.11, 206.21, 206.29, 128/207.13, DIG. 26
See application file for complete search history.

(56) References Cited

U.S. PATENT DOCUMENTS

| | | | | |
|---|---|---|---|---|
| 3,802,431 A | * | 4/1974 | Farr ..................... | 128/207.18 |
| 4,156,426 A | * | 5/1979 | Gold ..................... | 128/204.18 |
| 5,046,491 A | * | 9/1991 | Derrick ................. | 128/200.24 |
| 7,004,170 B1 | * | 2/2006 | Gillstrom .............. | 128/207.18 |
| 2005/0011523 A1 | * | 1/2005 | Aylsworth et al. ..... | 128/207.18 |
| 2005/0257794 A1 | * | 11/2005 | Aylsworth et al. ..... | 128/207.18 |
| 2005/0284484 A1 | * | 12/2005 | Curti et al. ............ | 128/207.18 |
| 2006/0042638 A1 | * | 3/2006 | Niklewski et al. ...... | 128/207.18 |
| 2006/0169281 A1 | * | 8/2006 | Aylsworth et al. ..... | 128/204.23 |

* cited by examiner

*Primary Examiner*—Justine R Yu
*Assistant Examiner*—Clinton Ostrup
(74) *Attorney, Agent, or Firm*—Trojan Law Offices

(57) ABSTRACT

A nasal cannula and mouthpiece assembly for delivering oxygen to a person is provided having a nasal cannula, at least two mouthpieces, two pairs of oxygen supply tubes and two sets of adjustors. Each mouthpiece has a first outer end for receiving oxygen and a second outer end with a first and second opening. The first opening delivers oxygen across lips of a mouth of the person and the second opening delivers oxygen inside the mouth from the sides. A sleeve member encloses each of the mouthpieces and positions the mouthpieces in front of the sides of the mouth. The oxygen supply tubes of the first pair deliver oxygen to the nasal cannula and those of the second pair deliver oxygen to the first pair and to the mouthpieces. The two sets of adjustors adjust the lengths of the oxygen supply tubes of the first pair and the mouthpieces to provide a desired fit of the assembly on the person.

18 Claims, 3 Drawing Sheets

NASAL CANULA AND MOUTHPIECE ASSEMBLY AND METHOD

FIELD OF THE INVENTION

This invention relates to a nasal cannula and mouthpiece assembly, and more particularly, to a nasal cannula and mouthpiece assembly for delivering oxygen to a person.

BACKGROUND OF THE INVENTION

Oxygen is an essential gas that is absolutely necessary for human survival. Each person requires a steady dose of oxygen. When a person's oxygen saturation in his or her bloodstream is less than about ninety-one percent, he or she risks suffering from brain damage and respiratory arrest, among other ailments, including delerium, caused by the oxygen deprivation.

Receiving a steady dose of oxygen is problematic for people with respiratory problems, especially during sleeping hours. Various oxygen delivery devices have been introduced, including nasal cannulas and oxygen masks, both of which assist the person by supplying oxygen and, therefore, require him or her to expend less energy to breathe. However, both nasal cannulas and oxygen masks have many significant drawbacks, especially when worn for a prolonged period of time and in particular during sleeping hours.

Known oxygen masks cover both a person's nose and mouth and include a bag that fills up with oxygen (FIG. 4). When a person inhales while wearing a known mask, the mask exhibits suction, resulting in severe pressure and tightness around the person's face. The tightness causes extreme discomfort for people, especially during the sleeping hours, when, as a result of being in a dreamed state of mind, the mask wearer panics and believes that he or she is suffocating. This panic causes the person to remove the mask in order to obtain relief from the unbearable tightness and pressure caused by the mask. Unfortunately, when a person with respiratory problems removes the mask, he or she consequently does not receive enough oxygen and, accordingly, becomes delirious and suffers from respiratory arrest and, in some instances, death.

The risk of death is heightened by those people under the care and supervision of medical personnel, including nurses and respiratory therapists, who are forbidden by laws to use restraints to prevent a panicked person from removing an oxygen mask without a doctor's permission. Consequently, these medical personnel must physically restrain such persons with their own effects. In most instances, because the respiratory patient has become delirious as a result of the oxygen deprivation, he or she falsely believes that the nurse or respiratory therapist is attempting to hurt him or her and consequently fights back. Furthermore, there is usually a low ratio of medical personnel to respiratory patients in such facilities, especially during sleeping hours, thereby compounding the risk of death. This is because as one nurse or respiratory therapist is physically restraining a patient who has removed a mask in one room, he or she cannot attend to other patients in neighboring rooms who are also removing their oxygen masks and who consequently suffer and die as a result of removal of the known oxygen mask that caused the extreme discomfort that necessitated its removal. A need, therefore, exists for an oxygen delivery device that delivers a steady dose of oxygen to a person and that does not cause extreme discomfort when worn for a prolonged period of time, especially during sleeping hours.

Although known nasal cannulas are less restricting than oxygen support masks, nasal cannulas do not deliver oxygen to a person's mouth and, therefore, do not deliver an effective dose of oxygen when used alone. Further, known nasal cannulas cause discomfort when they do not (or cannot be adjusted to) properly fit an individual person's face. Therefore, a need exits for an oxygen delivery system that delivers a steady dose of oxygen to both a person's nasal and oral cavities and that is also adjustable so that it is capable of properly fitting a variety of different people's faces.

SUMMARY OF THE INVENTION

In accordance with the present invention, a nasal cannula and mouthpiece assembly for delivering oxygen to a person is provided that includes a nasal cannula, at least two mouthpieces, at least two rigid sleeve members, a first and second pair of oxygen supply tubes and a first and second set of adjustors. The nasal cannula and mouthpiece assembly, when properly adjusted to fit on a person's face, allows for a comfortable and non-restricting device that provides a steady stream of oxygen to the person.

In accordance with one aspect of the invention, in a preferred embodiment, the nasal cannula is a hollow tubular member having two ends with an oxygen supply opening at each end and two nasal prongs that insert into nostrils of the person. However, in carrying out the invention, any nasal cannula known in the art may be used.

In accordance with another aspect of the invention, each mouthpiece includes an oxygen supply tube and has two ends, a first outer end for receiving oxygen and a second outer end that further includes a first and second opening. The first opening delivers oxygen across the lips of the person's mouth and the second opening is a hollow oral prong approximately perpendicular to the first opening and is inserted into the side or corner of the person's mouth and delivers oxygen therein. The first and second openings provide oxygen both directly into the person's mouth and also across his or her lips and, thereby, ensure a sufficient stream of oxygen to be inhaled by the person.

In accordance with yet another aspect of the invention, a proper position of the mouthpieces is attained with sleeve members. Each sleeve member is preferably rigid and surrounds each mouthpiece and properly positions the mouthpieces in front of the sides of the mouth of the person.

In accordance with yet still another aspect of the invention, the first pair of oxygen supply tubes deliver oxygen to the nasal cannula. The oxygen supply tubes include two ends: a first end and a second end. Each oxygen supply tube is connected to the mouthpiece and the second pair of oxygen supply tubes at the first end and to the ends of the nasal cannula at the second end. In one embodiment, the second end may be integral with the ends of the nasal cannula. Further, in the preferred operative position of the assembly, the oxygen supply tubes are positioned above and behind the ears of the person.

In accordance with another aspect of the invention, the second pair of oxygen supply tubes deliver oxygen to the first pair of oxygen supply tubes and to the mouthpieces. The oxygen supply tubes of the second pair include two ends: a first end and a second end. Each oxygen supply tube of the second pair is connected to a main oxygen supply line at the first end and to the first pair of supply tubes and to the mouthpieces at the second end. In one embodiment, the first end of each oxygen supply tube of the second pair is integrally connected to an end of the main oxygen supply line.

In accordance with yet another aspect of the invention, in a preferred embodiment, at least two multi-prong connectors with hollow interiors facilitate connection of the first and second pairs of supply tubes and mouthpieces. In this embodiment, the first end of each oxygen supply tube of the first pair, the first outer end of each mouthpiece and the second end of each oxygen supply tube of the second pair include a sleeve portion of increased diameter for receiving a prong of the connector. In one embodiment, the second end of each oxygen supply tube of the second pair is integrally connected to a prong of the connector. However, a practitioner skilled in the art will understand that any similar connector with hollow interiors may be used to facilitate connection.

In accordance with yet still another aspect of the invention, in the preferred embodiment, the first set of adjustors adjust the length of the oxygen supply tubes of the first pair to provide a desired and proper fit of the nasal cannula on the person. Similarly, the second set of adjustors adjust the length of the mouthpieces to provide a desired and proper fit of the mouthpieces on the person. In the preferred embodiment, the adjustors include an inner member and a sleeve member and the width of the sleeve member is greater than the width of the inner member so that the inner member can be inserted into the interior of the sleeve member. Further, in the preferred embodiment, the sleeve member includes recesses that receive ribs of the inner member and as the inner member is inserted into the interior of the sleeve member, the ribs engage the recesses until a desired length is obtained. However, a practitioner skilled in the art will understand that the adjustors can be of any suitable structure and configuration that provides for a change of length. Alternately, the mouthpieces and oxygen supply tubes of the first pair can be of sufficient lengths to provide a desired and proper fit on the person, thereby eliminating a necessity for the adjustors.

In accordance with another aspect of the invention, in carrying out the invention, the assembly also includes a slip loop that surrounds the oxygen supply tubes of the second pair. Upon properly fitting the nasal cannula and mouthpieces on the person, the slip loop may be moved in a vertical direction along the oxygen supply tubes to further provide a desired and proper fit of the assembly around the neck of the person.

In accordance with yet another aspect of the invention, in carrying out the invention, the assembly is preferably made of flexible elastomeric material. However, the assembly can be made of any suitable lightweight, flexible and comfortable material as known in the art.

In accordance with yet still another aspect of the invention, a method of delivering oxygen to a person by applying the nasal cannula and mouthpiece assembly is also provided. The method includes positioning the nasal cannula in proximity to the nostrils of the person. The method further includes extending the first pair of oxygen supply tubes above and behind the ears of the person. The method still further includes adjusting the length of the first pair of oxygen supply tubes with the first set of adjustors to provide a desired and proper fit of the nasal cannula on the person. The method yet further includes positioning the mouthpieces with sleeve members in front of the sides of the person's mouth. The method yet still further includes inserting the oral prongs of the mouthpieces into the sides of the mouth. The method further includes adjusting the length of the mouthpieces to provide a desired and proper fit of the mouthpieces on the person. The method still further includes supplying oxygen to the main oxygen supply line, thereby supplying oxygen to the assembly and, consequently, to the person.

Numerous advantages may be realized by the present invention. For example, the assembly overcomes the drawbacks of known oxygen masks and delivers a steady dose of oxygen to a person's nasal and oral cavities without any extreme discomfort or facial restrictions while the assembly is worn for prolonged periods of time and especially during sleeping hours.

Other advantages and features of the invention will become apparent from the following description and from reference to the drawings.

DETAILED DESCRIPTION OF THE DRAWINGS

Figure 1:
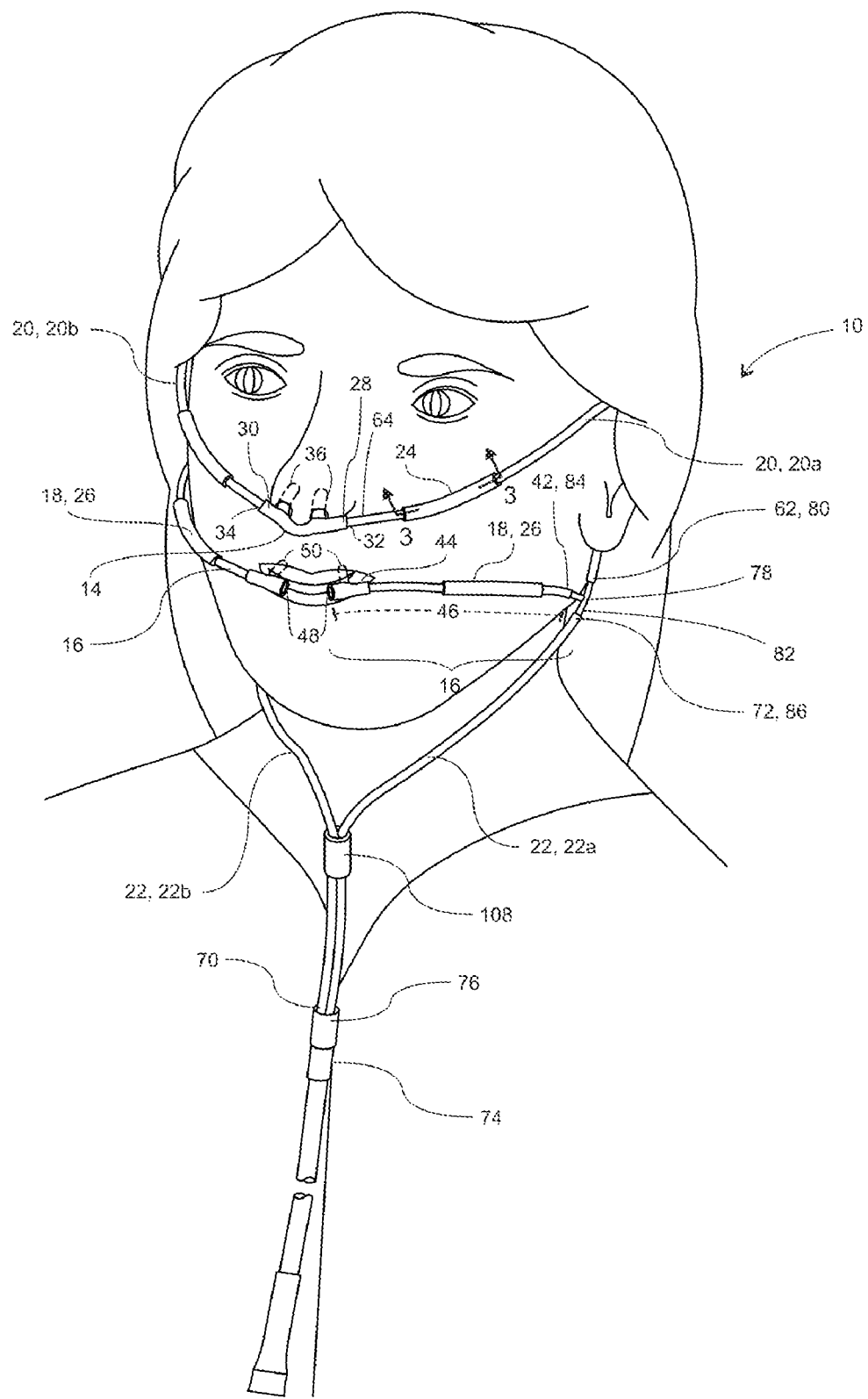
FIG. 1 illustrates a front elevation view of a nasal cannula and mouthpiece assembly in accordance with the present invention in an operative position properly fit on a person.
Figure 2:
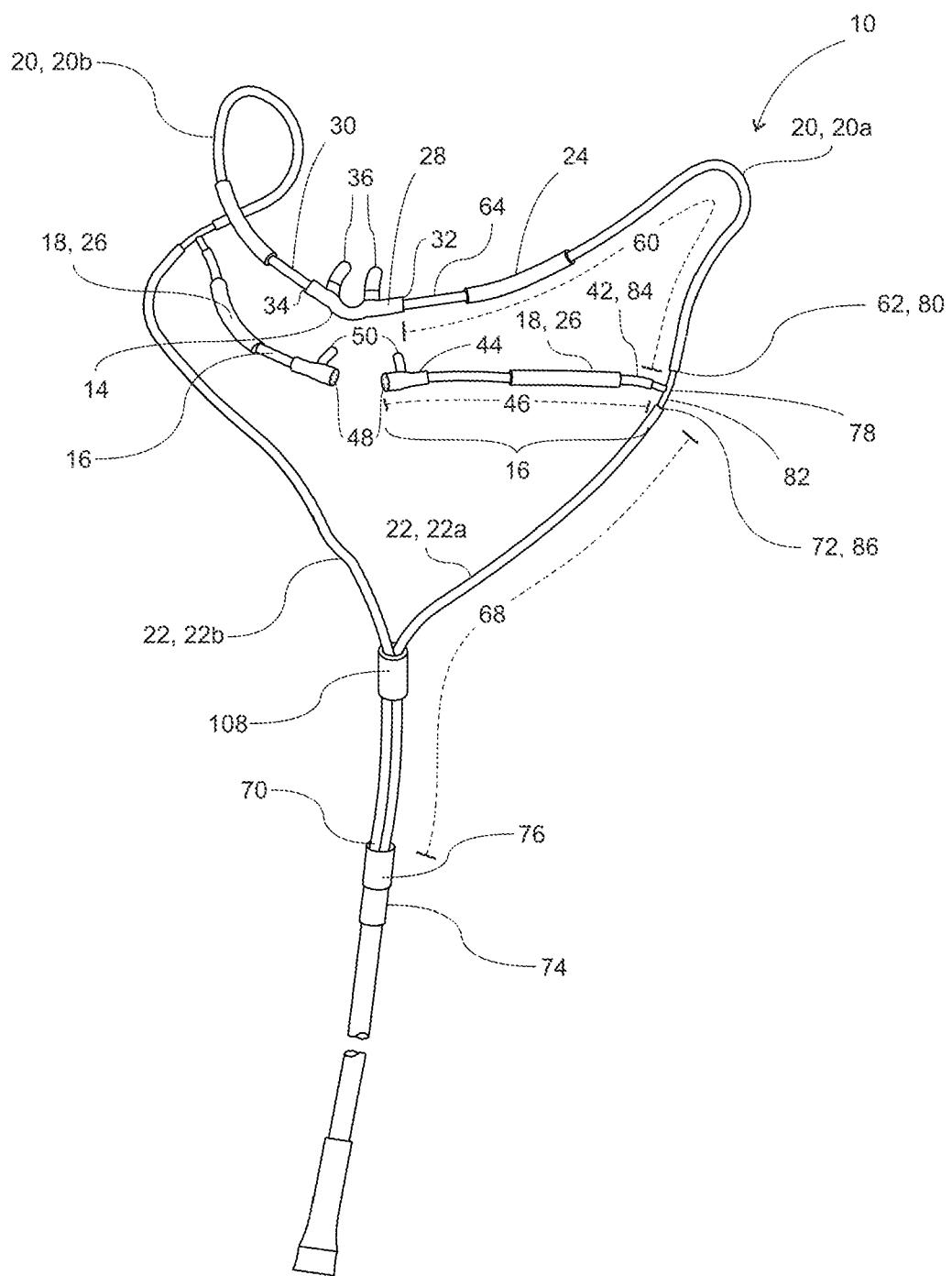
FIG. 2 illustrates a perspective view of the assembly of FIG. 1.

Referring to the figures generally, and in particular to FIGS. 1 to 2, where like numerals denote like elements, there is illustrated a nasal cannula and mouthpiece assembly 10 for delivering oxygen to a person in accordance with the invention. Nasal cannula and mouthpiece assembly 10 includes a nasal cannula 14, at least two mouthpieces 16, at least two sleeve members 18 surrounding mouthpieces 16, a first and second pair of oxygen supply tubes 20 and 22, respectively, and a first and second set of adjustors 24 and 26, respectively, to provide a proper fit of nasal cannula 14 and mouthpieces 16, respectively, on person.

In a preferred embodiment, nasal cannula 14 is a hollow tubular member having a first end 28, a second end 30, an oxygen supply opening at each end 32 and 34, respectively, and two nasal prongs 36 that insert into nostrils of person, as illustrated in FIGS. 1 and 2. In one embodiment, nasal prongs 36 are integral with nasal cannula 14. However, in carrying out the invention, any nasal cannula 14 known in the art may be used.

Each mouthpiece 16 includes an oxygen supply tube 40 and has a first outer end 42 for receiving oxygen, a second outer end 44, as illustrated in FIGS. 1 and 2 and a length 46, as illustrated in FIG. 2. Second outer end 44 further includes a first and second opening 48 and 50, respectively. First opening 48 delivers oxygen across lips of a mouth of person. Second opening 50 is a hollow oral prong approximately perpendicular to first opening 48 and is inserted into a side or corner of mouth of person and delivers oxygen therein. First and second openings 48 and 50 provide oxygen both directly into mouth of person and also across his or her lips and, thereby, ensure a sufficient stream of oxygen to be inhaled by person. However, to ensure a sufficient stream of oxygen into mouth from both sides of mouth, both mouthpieces 16 must be properly positioned and fit onto person.

In the illustrated embodiment, a proper position of mouthpieces 16 is attained with sleeve members 18, as illustrated in FIGS. 1 and 2. Each sleeve member 18 is preferably rigid and surrounds each mouthpiece 16 and properly positions mouthpiece 16 in front of side of mouth of person, as best illustrated in FIG. 1. However, any other similar positioning member known in the art may be used to properly position mouthpieces 16. For example, in one embodiment (not shown), mouthpieces 16 may be made of rigid material, thereby relieving the necessity for rigid sleeve members 18.

In an alternate embodiment (not shown), mouthpieces 16 include only one opening, first opening 48, which delivers oxygen across lips of mouth of person and eliminates second opening 50 inserts. This embodiment is preferably used for a person who has sensitive skin or otherwise desires to prevent any chafing or deterioration of the skin at sides of mouth. In another alternate embodiment (not shown), only one mouthpiece 16 is included. This embodiment may be used, for example, with a person that sleeps on his or her side and, therefore, desires to eliminate any possible pressure caused by second mouthpiece 16.

First pair 20 of oxygen supply tubes 20a and 20b deliver oxygen to nasal cannula 14, as illustrated in FIGS. 1 and 2. Oxygen supply tubes 20a and 20b include a length 60, a first end 62 and a second end 64. Each oxygen supply tube 20a and 20b is connected to mouthpiece 16 and second pair 22 of oxygen supply tubes 22a and 22b at first end 62 and to first and second ends 28 and 30, respectively, of nasal cannula 14 at second end 64. In one embodiment, second end 64 may be integral with first and second ends 28 and 30, respectively. However, a practitioner skilled in the art will understand that any attachment methods known in the art may be used, so long as the interiors remain hollow to allow oxygen to flow therein. In the preferred operative position of assembly 10, oxygen supply tubes 20a and 20b are positioned above and behind ears of person, as illustrated in FIG. 1.

Second pair 22 of oxygen supply tubes 22a and 22b deliver oxygen to first pair 20 of oxygen supply tubes 20a and 20b and to mouthpieces 16, as illustrated in FIGS. 1 and 2. Oxygen supply tubes 22a and 22b include a length 68, a first end 70 and a second end 72. Each oxygen supply tube 22a and 22b of second pair 22 is connected to a main oxygen supply line 74 at first end 70 and to first pair 20 of supply tubes 20a and 20b and to mouthpieces 16 at second end 72. In one embodiment, first end 70 of each oxygen supply tube 22a and 22b of second pair 22 is integrally connected to an end 76 of said main oxygen supply line 74. However, a practitioner skilled in the art will understand that any attachment methods known in the art may be used, so long as the interiors remain hollow to allow oxygen to flow therein.

In a preferred embodiment, at least two multi-prong connectors 78 with hollow interiors (not shown) facilitate connection of first and second pairs 20 and 22, respectively, of supply tubes 20a, 20b and 22a and 22b, respectively, and mouthpieces 16, as illustrated in FIGS. 1 and 2. In this embodiment, first end 62 of each oxygen supply tube 20a and 20b of first pair 20 includes a sleeve portion 80 of increased diameter for receiving a prong 82 of connector 78. Further, in this embodiment, first outer end 42 of each mouthpiece 16 includes a sleeve portion 84 of increased diameter for receiving a prong 82 of connector 78. Still further, second end 72 of each oxygen supply tube 22a and 22b of second pair 22 includes a sleeve portion 86 of increased diameter for receiving a prong 82 of connector 76. In one embodiment, second end 72 of each oxygen supply tube 22a and 22b of second pair 22 is integrally connected to prong 82 of connector 78. However, a practitioner skilled in the art will understand that any connector known in the art may be used, so long as the interiors remain hollow to allow oxygen to flow therein.

First set of adjustors 24 adjust length 60 of oxygen supply tubes 20a and 20b to provide a desired and proper fit of nasal cannula 14 on person. Second set of adjustors 26 adjust length 46 of mouthpieces 16 to provide a desired and proper fit of mouthpieces 16 on person. The illustrated embodiment of FIGS. 1 and 2 discloses that second set of adjustors 26 is the same as rigid sleeve members 18. Although one section of mouthpiece 16 can perform both functions, alternately, second set of adjustors 26 and rigid sleeve members 18 can be distinct sections of mouthpiece 16.

Figure 3:
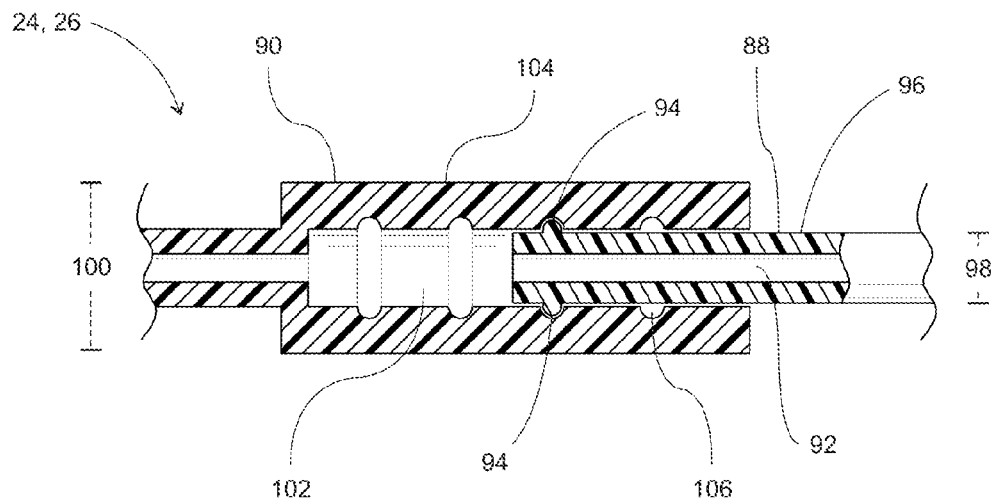
FIG. 3 illustrates a sectional elevation view of the assembly taken along line 3-3 of FIG. 1.

FIG. 3 illustrates a preferred embodiment of sets of adjustors 24 and 26. In this embodiment, adjustors 24 and 26 include an inner member 88 and a sleeve member 90. Inner member 88 has a hollow interior 92, ribs 94 on exterior 96 and a width 98. Sleeve member 90 has a width 100, an interior 102 and an exterior 104. Width 100 of sleeve member 90 is greater than width 98 of inner member 88 so that inner member 88 can be inserted into interior 102 of sleeve member 90. Further, in the preferred embodiment, sleeve member 90 includes recesses 106 that receive ribs 94 of inner member. To obtain a desired and proper fit of both nasal cannula 14 and mouthpieces 16, inner member 88 is inserted into interior 102 of sleeve member 90 and ribs 94 engage recesses 106 until a desired length is obtained, as best illustrated in FIG. 3. However, a practitioner skilled in the art will understand that adjustors 24 and 26 can be of any suitable structure and configuration that provides for a change of lengths 60 and 46, respectively.

In an alternate embodiment (not shown), adjustors 24 and 26 are not included and instead, lengths 60 and 46 of first pair 20 of supply tubes 20a and 20b and mouthpieces 16 can be sufficient to properly fit person.

A slip loop 108 that surrounds oxygen supply tubes 22a and 22b of second pair 22 may also be provided, as illustrated in FIGS. 1 and 2. Upon properly fitting nasal cannula 14 and mouthpieces 16 on person, slip loop 108 may be moved in a vertical direction along oxygen supply tubes 22a and 22b to further provide a desired and proper fit of assembly 10 around neck of person, as best illustrated in FIG. 1.

In carrying with the invention, assembly 10 is preferably made of flexible elastomeric material. However, assembly 10 can be made of any suitable lightweight, flexible and comfortable material as known in the art.

Figure 4:
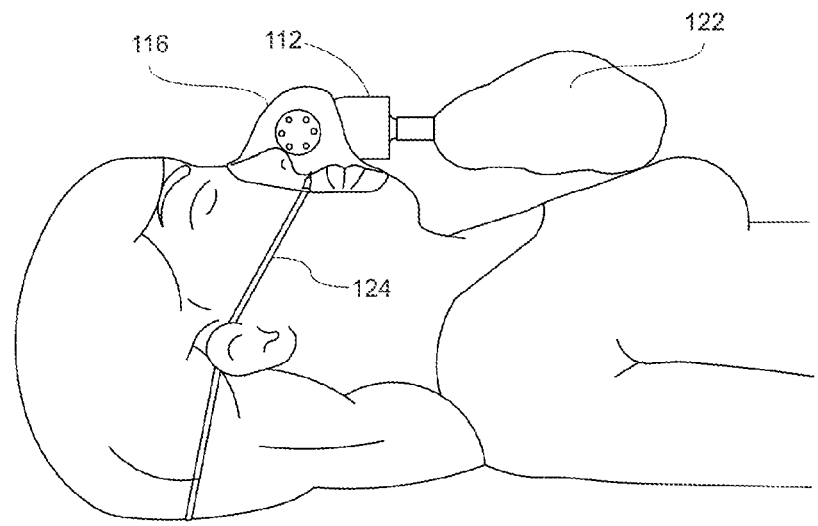
FIG. 4 illustrates a side view of a prior art oxygen mask in an operative position on a person.

Assembly 10 in accordance with the present invention overcomes many of the drawbacks of the prior art oxygen masks. FIG. 4 illustrates a known oxygen mask 112 fit on person. Known oxygen mask 112 includes a mask portion 116 that covers nose and mouth of person. Mask 112 also includes an oxygen bag 122 and strap 124 that fits around head of person. Known oxygen masks 112 cause extreme discomfort because of the severe pressure and tightness that results around face of person when person breathes while wearing mask 112. This extreme discomfort is especially felt when a person is wearing mask 112 for a prolonged period of time and especially during sleeping hours. Assembly 10 of the present invention overcomes the drawbacks of known oxygen mask 112 and delivers a steady dose of oxygen to person without any extreme discomfort or facial restrictions while assembly 10 is worn for prolonged periods of time or during sleeping hours.

To properly assemble nasal cannula and mouthpiece assembly 10 to deliver oxygen to person, one first positions nasal cannula 14 in proximity to nostrils of person. Next, to maintain nasal cannula 14 in position, first pair 20 of oxygen supply tubes 20a and 20b are extended above and behind ears of person. Then, one adjusts lengths 60 of first pair 20 of oxygen supply tubes 20a and 20b with first set of adjustors 24 to provide a desired fit of nasal cannula 14 on person. Next, one positions mouthpieces 16 with sleeve members 18 in front of sides of mouth of person. Then, oral prongs 56 are inserted into sides or corners of mouth. Next, one adjusts lengths 46 of mouthpieces 16 to provide a desired fit of mouthpieces 16 on person. Lastly, oxygen is supplied to main oxygen supply line 74, thereby supplying oxygen to assembly 10 and, consequently, to person.

While the invention has been described with respect to certain preferred embodiments, as will be appreciated by those skilled in the art, it is to be understood that the invention is capable of numerous changes, modifications and rearrangements and such changes, modifications and rearrangements are intended to be covered by the following claims.

I claim:

1. A nasal cannula and mouthpiece assembly for delivering oxygen to a person comprising:
   a nasal cannula;
   two mouthpieces, and wherein each of said mouthpieces comprises a tube having a first end for receiving oxygen and a second end, wherein said second end further comprises a first opening for delivering oxygen across lips of a mouth of said person and a second opening comprising a hollow oral prong projecting from a side of said second end for insertion into said person's mouth for delivery of oxygen therein;
   a first pair of oxygen supply tubes connecting each said first end of said two mouthpieces with an oxygen source for delivering oxygen to said two mouthpieces; and
   a second pair of oxygen supply tubes connecting said nasal cannula with an oxygen source for delivering oxygen to said nasal cannula,
   wherein said nasal cannula is separate from said two mouthpieces, whereby said person can independently adjust said nasal cannula and said two mouthpieces for providing a more comfortable fit of said nasal cannula and mouthpiece assembly.

2. The nasal cannula and mouthpiece assembly of claim 1 further comprising at least two sleeve members, wherein each sleeve member encloses each mouthpiece said two mouthpieces and is for positioning each said mouthpiece in front of sides of the mouth.

3. The nasal cannula and mouthpiece assembly of claim 1 further comprising a first set of adjustors for adjusting a length of said second pair of oxygen supply tubes for providing a desired fit of said nasal cannula on said person.

4. The nasal cannula and mouthpiece assembly of claim 3 further comprising a second set of adjustors for adjusting a length of said two mouthpieces for providing a desired fit of said two mouthpieces on said person.

5. The nasal cannula and mouthpiece assembly of claim 1 further comprising at least two multi-prong connectors with hollow interiors for facilitating connection of said first pair of oxygen supply tubes, said second pair of oxygen supply tubes, and said two mouthpieces.

6. The nasal cannula and mouthpiece assembly of claim 5 wherein an end of at least one of said second pair of oxygen supply tubes includes a sleeve portion of increased diameter for receiving a prong of said at least two multi-prong connectors.

7. The nasal cannula and mouthpiece assembly of claim 6 wherein said end of at least one of said first pair of oxygen supply tubes is integrally connected with said prong of said at least two multi-prong connectors.

8. The nasal cannula and mouthpiece assembly of claim 5 wherein said first end of each of said two mouthpieces includes a sleeve portion of increased diameter for receiving a prong of said at least two multi-prong connectors.

9. The nasal cannula and mouthpiece assembly of claim 1 wherein said nasal cannula comprises a hollow tubular member having an oxygen supply opening at each end and two nasal prongs integral with said tubular member for insertion into nostrils of said person.

10. The nasal cannula and mouthpiece assembly of claim 1 wherein an end of at least one of said second pair of oxygen supply tubes is integrally connected with an outer end of said nasal cannula.

11. The nasal cannula and mouthpiece assembly of claim 1 further comprising a slip loop that surrounds said first pair of oxygen supply tubes for providing a desired fit of said nasal cannula and mouthpiece assembly on a neck of said person.

12. The nasal cannula and mouthpiece assembly of claim 1 wherein at least one end of at least one of said first pair of oxygen supply tubes is integrally connected with an end of a main oxygen supply line connected with said oxygen source.

13. The nasal cannula and mouthpiece assembly of claim 1 wherein said nasal cannula and mouthpiece assembly is comprised of flexible elastomeric material.

14. A nasal cannula and mouthpiece assembly for delivering oxygen to a person comprising:
   a nasal cannula comprising a hollow tubular member having an oxygen supply opening at each end and two nasal prongs integral with said tubular member for insertion into nostrils of said person;
   at least two mouthpieces, wherein each of said mouthpieces comprises a first outer end having a sleeve portion of increased diameter for connecting with an oxygen supply tube for receiving oxygen and a second outer end with at least two openings, one of which is for delivering oxygen across the lips of said person and the other is for delivering oxygen directly into the mouth of said person;
   at least two sleeve members, wherein each sleeve member encloses each of said at least two mouthpieces and is for positioning said at least two mouthpieces in front of sides of said mouth;
   a first pair of oxygen supply tubes for delivering oxygen to said nasal cannula, wherein said first pair of oxygen supply tubes are for placement above and behind ears of said person and wherein each oxygen supply tube of said first pair of oxygen supply tubes includes a first end that is integrally connected with said ends of said nasal cannula and a second end having a sleeve portion of increased diameter for connecting with a mouthpiece of said at least two mouthpieces and an oxygen supply tube of a second pair of oxygen supply tubes;
   a first set of adjusters for adjusting a length of said oxygen supply tube of said first pair of oxygen supply tubes for providing a desired fit of said nasal cannula on said person;
   wherein said second pair of oxygen supply tubes delivers oxygen to said first pair of oxygen supply tubes and to said at least two mouthpieces and wherein each oxygen supply tube of said second pair of oxygen supply tubes includes a first end that is integrally connected with a main oxygen supply line and a second end having a sleeve portion of increased diameter for connecting with a mouthpiece of said at least two mouthpieces and an oxygen supply tube of said first pair of oxygen supply tubes;
   a second set of adjustors for adjusting a length of said at least two mouthpieces for providing a desired fit of said at least two mouthpieces on said person;
   at least two multi-prong connectors with hollow interiors for facilitating connection of said first and second pairs of oxygen supply tubes and said at least two mouthpieces; and
   a slip loop that surrounds said oxygen supply tubes of said second pair of oxygen supply tubes for providing a desired fit of said nasal cannula and mouthpiece assembly on a neck of said person.

15. The nasal cannula and mouthpiece assembly of claim 14 wherein said second end of each of said oxygen supply tubes of said second pair of oxygen supply tubes is integrally connected with a prong of said at least two multi-prong connectors.

16. The nasal cannula and mouthpiece assembly of claim 14 wherein said nasal cannula and mouthpiece assembly is comprised of flexible elastomeric material.

17. A nasal cannula and mouthpiece assembly for delivering oxygen to a person comprising:
   a nasal cannula;
   at least two mouthpieces, wherein each mouthpiece of said at least two mouthpieces comprises a first outer end for receiving oxygen and a second outer end with a first and second opening, wherein said first opening is capable of delivering oxygen across the lips of said person and said second opening comprises a hollow oral prong for insertion into a mouth of said person;
   a first pair of oxygen supply tubes, wherein each oxygen supply tube of said first pair of oxygen supply tubes is connected with one of said at least two mouthpieces and one oxygen supply tube of a second pair of oxygen supply tubes at a first end, and with said nasal cannula at a second end; and
   wherein each oxygen supply tube of said second pair of oxygen supply tubes is connected with a main oxygen supply line at a first end, and with one oxygen supply tube of said first pair of oxygen supply tubes and with one of said at least two mouthpieces at a second end;
   wherein said nasal cannula is separate from said two mouthpieces,
   whereby said person can independently position said nasal cannula and said two mouthpieces for providing a more comfortable fit of said nasal cannula and mouthpiece assembly on said person.

18. A method of delivering oxygen to a person by applying a nasal cannula and mouthpiece assembly, the assembly having a nasal cannula; at least two mouthpieces, wherein each mouthpiece of said at least two mouthpieces comprises a first outer end for receiving oxygen and a second outer end with a first and second opening, wherein said first opening delivers oxygen across the lips of said person and said second opening comprises a hollow oral prong capable of being inserted into a mouth of said person; at least two sleeve members, wherein each sleeve member surrounds each said mouthpiece of said at least two mouthpieces; a first pair of oxygen supply tubes, wherein each oxygen supply tube of said first pair of oxygen supply tubes is connected with a mouthpiece of said at least two mouthpieces and an oxygen supply tube of a second pair of oxygen supply tubes at a first end and to said nasal cannula at a second end; a first set of adjustors for adjusting said first pair of oxygen supply tubes, wherein each oxygen supply tube of said second pair of oxygen supply tubes is connected with a main oxygen supply line at a first end and to an oxygen supply tube of said first pair of oxygen supply tubes and to a mouthpiece of said at least two mouthpieces at a second end and a second set of adjustors for adjusting said at least two mouthpieces, the method comprising the steps of:
   positioning said nasal cannula with a nose of said person;
   extending said first pair of oxygen supply tubes above and behind ears of said person;
   adjusting a length of said first pair of oxygen supply tubes with said first set of adjustors to provide a desired fit of said nasal cannula on said person;
   positioning said at least two mouthpieces with rigid sleeve members in front of sides of said mouth of said person;
   inserting said oral prongs into said sides of said mouth;
   adjusting a length of said at least two mouthpieces to provide a desired fit of said at least two mouthpieces on said person; and
   supplying oxygen to said main oxygen supply line.

* * * * *